(12) United States Patent
Hei et al.

(10) Patent No.: US 11,805,861 B2
(45) Date of Patent: *Nov. 7, 2023

(54) FOOT MEASURING AND SIZING APPLICATION

(71) Applicant: NIKE, Inc., Beaverton, OR (US)

(72) Inventors: Joseph Hei, Palo Alto, CA (US); Vivian Chiang, Palo Alto, CA (US); Jason Warren, Taipei (TW)

(73) Assignee: NIKE, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/574,275

(22) Filed: Jan. 12, 2022

(65) Prior Publication Data
US 2022/0202138 A1 Jun. 30, 2022

Related U.S. Application Data

(63) Continuation of application No. 16/791,572, filed on Feb. 14, 2020, now Pat. No. 11,324,285, which is a (Continued)

(51) Int. Cl.
A43D 1/02 (2006.01)
A61B 5/00 (2006.01)
(Continued)

(52) U.S. Cl.
CPC ............ A43D 1/025 (2013.01); A61B 5/0022 (2013.01); A61B 5/0077 (2013.01);
(Continued)

(58) Field of Classification Search
None
See application file for complete search history.

(56) References Cited

U.S. PATENT DOCUMENTS 5,164,793 A 11/1992 Wolfersberger et al.
5,689,446 A 11/1997 Sundman et al.
(Continued)

FOREIGN PATENT DOCUMENTS

CN 101707946 A 5/2010
CN 101742048 A 6/2010
(Continued)

OTHER PUBLICATIONS

Oct. 1, 2018—(WO) ISR & WO—App. No. PCT/US18/039781.
(Continued)

Primary Examiner — Christopher W Fulton
(74) Attorney, Agent, or Firm — Banner & Witcoff, Ltd.

(57) ABSTRACT

Systems and processes for measuring and sizing a foot are provided. In one exemplary process, at least one image of a foot and a horizontal reference object from a first point of view is captured. A portion of the foot may be disposed against a vertical reference object. The at least one image may be displayed, where one or more camera guides are overlaid on the at least one displayed image. In response to aligning the one or more camera guides with one or more of the horizontal reference object and the vertical reference object, a measurement of the foot based on the at least one captured image from the first point of view is determined.

20 Claims, 11 Drawing Sheets

Related U.S. Application Data continuation of application No. 15/796,457, filed on Oct. 27, 2017, now abandoned, which is a continuation-in-part of application No. 15/699,861, filed on Sep. 8, 2017, now Pat. No. 10,420,397.

(60) Provisional application No. 62/434,151, filed on Dec. 14, 2016.

(51) Int. Cl.
  *G06Q 30/0601*    (2023.01)
  *G06Q 30/06*    (2023.01)
  *G06T 7/521*    (2017.01)
  *A61B 5/107*    (2006.01)
  *G06T 7/62*    (2017.01)

(52) U.S. Cl.
  CPC .......... *A61B 5/1074* (2013.01); *A61B 5/1079* (2013.01); *A61B 5/6898* (2013.01); *G06Q 30/06* (2013.01); *G06Q 30/0627* (2013.01); *G06T 7/521* (2017.01); *G06T 7/62* (2017.01)

(56) References Cited

U.S. PATENT DOCUMENTS

| | | |
|---|---|---|
| 6,289,107 B1 | 9/2001 | Borchers et al. |
| 6,546,356 B1 | 4/2003 | Genest |
| 8,065,200 B2 | 11/2011 | Schwartz |
| 8,567,081 B2 | 10/2013 | Smith |
| 8,655,053 B1 | 2/2014 | Hansen |
| 8,818,883 B2 | 8/2014 | Lawrence et al. |
| 8,868,157 B1 | 10/2014 | Soliz |
| 8,908,928 B1 | 12/2014 | Hansen |
| 9,345,957 B2 | 5/2016 | Geisner et al. |
| 9,386,889 B2 | 7/2016 | Fischer |
| 9,462,838 B1 | 10/2016 | Smith et al. |
| 9,477,980 B2 | 10/2016 | Zagel et al. |
| 9,648,926 B2 | 5/2017 | Marks |
| 9,799,064 B2 | 10/2017 | Ohnemus et al. |
| 9,875,546 B1 | 1/2018 | Bhole et al. |
| 9,996,981 B1 | 6/2018 | Tran et al. |
| 10,008,040 B2 | 6/2018 | Lam et al. |
| 10,013,803 B2 | 7/2018 | Mach Shepherd et al. |
| 10,067,500 B2 | 9/2018 | Hargovan et al. |
| 10,380,794 B2 | 8/2019 | Hauswiesner et al. |
| 10,420,397 B2 | 9/2019 | Hei et al. |
| 10,573,004 B2 | 2/2020 | Husheer |
| 10,755,431 B2 | 8/2020 | Shea et al. |
| 11,324,285 B2 * | 5/2022 | Hei ............... A61B 5/0077 |
| 2004/0081336 A1 | 4/2004 | Brooks |
| 2006/0104503 A1 | 5/2006 | Huang et al. |
| 2007/0005174 A1 | 1/2007 | Thomas |
| 2007/0056212 A1 | 3/2007 | Fink |
| 2008/0040278 A1 | 2/2008 | DeWitt |
| 2009/0051683 A1 | 2/2009 | Goonetilleke et al. |
| 2009/0247909 A1 | 10/2009 | Mukumoto |
| 2009/0287452 A1 | 11/2009 | Stanley et al. |
| 2010/0111370 A1 | 5/2010 | Black et al. |
| 2010/0296726 A1 | 11/2010 | Rutschmann et al. |
| 2011/0093344 A1 | 4/2011 | Burke et al. |
| 2011/0298897 A1 | 12/2011 | Sareen et al. |
| 2012/0054041 A1 | 3/2012 | Williams |
| 2012/0249741 A1 | 10/2012 | Maciocci et al. |
| 2013/0100256 A1 | 4/2013 | Kirk et al. |
| 2013/0114869 A1 | 5/2013 | Hernandez Stark et al. |
| 2013/0246222 A1 | 9/2013 | Weerasinghe |
| 2013/0307851 A1 | 11/2013 | Hernandez Stark et al. |
| 2014/0040041 A1 | 2/2014 | Ohnemus et al. |
| 2014/0089134 A1 | 3/2014 | Linh et al. |
| 2014/0104395 A1 | 4/2014 | Rohaly et al. |
| 2014/0108208 A1 | 4/2014 | Piana |
| 2014/0156449 A1 | 6/2014 | Ganesan et al. |
| 2014/0176565 A1 | 6/2014 | Adeyoola et al. |
| 2014/0270540 A1 | 9/2014 | Spector et al. |
| 2014/0285646 A1 | 9/2014 | Kahlon |
| 2014/0358738 A1 | 12/2014 | Ohnemus et al. |
| 2015/0012380 A1 | 1/2015 | Bank et al. |
| 2015/0039422 A1 | 2/2015 | Abraham et al. |
| 2015/0066707 A1 | 3/2015 | Unger et al. |
| 2015/0066712 A1 | 3/2015 | Altieri |
| 2015/0127132 A1 | 5/2015 | Nyong'o et al. |
| 2015/0127363 A1 | 5/2015 | Nyong'o et al. |
| 2015/0154453 A1 | 6/2015 | Wilf |
| 2015/0223730 A1 | 8/2015 | Ferrantelli |
| 2015/0228084 A1 | 8/2015 | Belyaev et al. |
| 2015/0258431 A1 | 9/2015 | Stafford et al. |
| 2015/0328016 A1 | 11/2015 | Summit et al. |
| 2015/0339752 A1 | 11/2015 | Chetuparambil et al. |
| 2015/0342266 A1 | 12/2015 | Cooper et al. |
| 2015/0359461 A1 | 12/2015 | Alfaro et al. |
| 2016/0063613 A1 | 3/2016 | Zhao et al. |
| 2016/0071143 A1 | 3/2016 | Pokorney et al. |
| 2016/0081435 A1 | 3/2016 | Marks |
| 2016/0093085 A1 | 3/2016 | Ray et al. |
| 2016/0110479 A1 | 4/2016 | Li |
| 2016/0125499 A1 | 5/2016 | Gooch et al. |
| 2016/0180391 A1 | 6/2016 | Zabaneh |
| 2016/0183879 A1 | 6/2016 | Goldish et al. |
| 2016/0247017 A1 | 8/2016 | Sareen et al. |
| 2016/0286906 A1 | 10/2016 | Malal et al. |
| 2016/0350833 A1 | 12/2016 | Andon |
| 2016/0367191 A1 | 12/2016 | Esposito et al. |
| 2017/0004568 A1 | 1/2017 | Radner |
| 2017/0027477 A1 | 2/2017 | Charles et al. |
| 2017/0056212 A1 | 3/2017 | Jonsson et al. |
| 2017/0076011 A1 | 3/2017 | Gannon |
| 2017/0083971 A1 | 3/2017 | Ray et al. |
| 2017/0169571 A1 | 6/2017 | Hung et al. |
| 2017/0208245 A1 | 7/2017 | Castillo et al. |
| 2017/0272728 A1 | 9/2017 | Rafii et al. |
| 2017/0323299 A1 | 11/2017 | Davis |
| 2018/0033202 A1 | 2/2018 | Lam et al. |
| 2018/0035762 A1 | 2/2018 | Towns et al. |
| 2018/0160776 A1 | 6/2018 | Hei et al. |
| 2018/0160777 A1 | 6/2018 | Hei et al. |
| 2018/0182091 A1 | 6/2018 | MacKinnon et al. |
| 2018/0240238 A1 | 8/2018 | Husheer |
| 2018/0247426 A1 | 8/2018 | Gluck et al. |
| 2018/0300445 A1 | 10/2018 | Schouwenburg et al. |
| 2018/0300791 A1 | 10/2018 | Ganesan et al. |
| 2019/0037134 A1 | 1/2019 | Merati |
| 2019/0082794 A1 | 3/2019 | Liu |
| 2019/0139252 A1 | 5/2019 | Zaiss et al. |
| 2019/0188784 A1 | 6/2019 | Bleicher et al. |
| 2021/0093050 A1 * | 4/2021 | Lee ............... A43D 1/025 |
| 2022/0183424 A1 * | 6/2022 | Nevala ............ A43D 1/025 |

FOREIGN PATENT DOCUMENTS

| | | |
|---|---|---|
| CN | 101819663 A | 9/2010 |
| CN | 102682395 A | 9/2012 |
| CN | 103093543 A | 5/2013 |
| CN | 103597519 A | 2/2014 |
| CN | 103852130 A | 6/2014 |
| CN | 104040580 A | 9/2014 |
| CN | 104170519 A | 11/2014 |
| JP | H06149376 A | 5/1994 |
| JP | 2000515088 A | 11/2000 |
| JP | 2001001272 A | 4/2001 |
| JP | 2002203167 A | 7/2002 |
| JP | 2003127994 A | 5/2003 |
| JP | 2003331108 A | 11/2003 |
| JP | 2005169015 A | 6/2005 |
| JP | 2007526028 A | 9/2007 |
| JP | 2010510587 A | 4/2010 |
| JP | 2013050937 A | 3/2013 |
| JP | 2013097799 A | 5/2013 |
| JP | 2014040231 A | 3/2014 |
| JP | 2016001360 A | 1/2016 |
| JP | 2016040649 A | 3/2016 |
| JP | 2016532197 A | 10/2016 |
| JP | 201779809 A | 5/2017 |
| KR | 20100019067 A | 2/2010 |
| KR | 20100131404 A | 12/2010 |

(56) References Cited

FOREIGN PATENT DOCUMENTS

| | | |
|---|---|---|
| KR | 20120123842 A | 11/2012 |
| KR | 20120123845 A | 11/2012 |
| KR | 20130052159 A | 5/2013 |
| KR | 20150061089 A | 6/2015 |
| KR | 20150070459 A | 6/2015 |
| KR | 20160005977 A | 1/2016 |
| KR | 20160021118 A | 2/2016 |
| WO | 9748027 A1 | 12/1997 |
| WO | 2005006905 A1 | 1/2005 |
| WO | 2012072844 A1 | 6/2012 |
| WO | 2013026798 A1 | 2/2013 |
| WO | 2014159726 A1 | 10/2014 |
| WO | 2016051416 A1 | 4/2016 |
| WO | 2017127132 A1 | 7/2017 |
| WO | 2018048902 A1 | 3/2018 |
| WO | 2018109421 A1 | 6/2018 |

OTHER PUBLICATIONS

Jul. 9, 2019—(WO) ISR & WO—App. No. PCT/US19/014958.
Nov. 16, 2017—(WO) ISR & WO—App. No. PCT/US17/050281.
May 24, 2018—(WO) ISR & WO—App. No. PCT/IB18/050041.
Sep. 21, 2021—(WO) ISR & WO—App. No. PCT/US21/034932.
Anonymous: "How to Calculate Height of Android Phone from ground—Stack Overflow". Aug. 17, 2017 (Aug. 17, 2017), XP055836361, Retreived from the Internet: URL:https://stackoverflow.com/questions/17443936/how-to-calculate-height-of-android-phone-from-ground [retreived on Aug. 31, 2021].

* cited by examiner

FOOT MEASURING AND SIZING APPLICATION

CROSS-REFERENCE TO RELATED APPLICATIONS

This application is a continuation of U.S. patent application Ser. No. 16/791,572, entitled "FOOT MEASURING AND SIZING APPLICATION," filed on Feb. 14, 2020, and now granted as U.S. Pat. No. 11,324,285, which is a continuation of U.S. patent application Ser. No. 15/796,457, entitled "FOOT MEASURING AND SIZING APPLICATION," filed on Oct. 27, 2017, now abandoned, which is a continuation-in-pail of U.S. patent application Ser. No. 15/699,861, entitled "FOOT MEASURING AND SIZING APPLICATION," filed on Sep. 8, 2017, and now granted as U.S. Pat. No. 10,420,397, which claims priority to U.S. Provisional Ser. No. 62/434,151, entitled "FOOT MEASURING AND SIZING APPLICATION," filed on Dec. 14, 2016. The contents of each of these applications are hereby incorporated by reference in their entireties for all purposes.

FIELD

The present invention relates generally to foot-sizing applications. More particularly, and in one aspect, the invention relates to a foot measuring application running on a mobile computing device with an integrated camera that can quickly and accurately inform the user the dimensions of the foot being measured through an image capture process, and give accurate and real-time feedback during the measuring process.

BACKGROUND

Traditionally, the size of a foot is determined by a physical device, such as a "Brannock" device, which is common in many footwear stores. A Brannock device includes a sliding element to line up with the forward edge of a toe, where a heel of the foot is braced against an opposite end of the device. This same device can also measure foot width with a separate sliding element.

One advantage of these traditional devices is that the user, or those accompanying the user, can see the dimensions generated in real-time. These individuals can agree with the measurements, dispute them, attempt further adjustment of the sliding elements or foot position, and therefore, adjust the foot measurements.

Without a physical measuring device, traditional foot measuring involves a process of trial and error to determine an appropriate shoe size. This process involves obtaining shoes of varying sizes so that the customer can try on each shoe and determine an optimal fit. This traditional method depends on feedback from the user in reaction to different physical shoes. Such trial and error can be especially challenging with children, or those who have physical disabilities or other impairments that make it challenging to gauge accurate feedback from the user.

Furthermore, a less common method of physical size determination is the use of special shoes with the forefoot constructed from clear or transparent materials. This method allows for the toe area to be viewed through the shoe. Similarly, the goal with this method is real-time feedback for the user to gauge accurate foot size. However, the main deficiency is the requirement that all different shoe styles and sizes include clear or transparent materials.

As consumers continue to move to online shopping for shoes, there is a growing interest in alternate methods of foot-sizing that are not dependent on such traditional methods of physical devices or shoes. One alternative method includes providing directions to a user to trace an outline of a target foot on a piece of paper and choose two points on the resulting contour to generate a linear measurement. Problems with this method include demanding too much time and effort from the user, dependency on the accuracy of the traced contour, and user understanding of how to measure the resulting contour itself Furthermore, many consumers do not wish to be bothered by this process, may draw an inaccurate outline (e.g., by drawing at an angle instead of vertical), or may incorrectly measure the traced outline (e.g., by not measuring along the major longitudinal axis of the foot).

Another alternative method includes using an application on "multi-touch" device having a relatively large screen, such as a tablet computer. These applications attempt to measure foot size by having the user place the target foot on the screen, while the tablet is situated on the ground with the screen facing up. Problems with this method include inability to measure feet that are larger than the screen, inability to capture features which are not at ground/screen level and that affect the measured maximum size (for example, a heel that juts out higher on the foot), and user sensitivity to device damage by stepping on the device.

Another alternative method includes an application that attempts to measure foot size by utilizing a camera built into the computing device. These applications may use a reference object of a known size (e.g., a coin) in the same field of view and obtain a picture of the foot along with the reference object. Problems with these applications include inaccuracy based on flawed processing techniques and algorithms, unacceptably long processing times if the image or multiple images are sent to a remote server for processing, and the lack of real-time feedback to the user.

Another class of alternative methods include applications which attempt to scan an entire foot and record 3D features of the foot, or by constructing a 3D digital model of the foot through multiple images. In addition to suffering from even longer processing times than the above methods due to the greater amount of data in a 3D calculation, there are doubts about the accuracy of the data generated given the complexity of the full-foot 3D model and reliance on in-situ consumer electronics and settings (e.g., lighting, background differences, etc.). This 3D-based method is also impractical given the limited commercially viable ways to convert a full 3D digital map of a foot to a completely custom shoe. Three-dimensional printing of shoes mapped to a custom 3D database is not yet viable as a mass-consumer option due to a number of issues, including the availability of shoe materials that are also available for 3D printing (e.g., specific materials for flexibility and durability), and the processing time needed to print an object the size of a shoe.

Therefore, a need exists in the field for a foot measuring application that can both provide real-time feedback to a user and provide an accurate determination of foot size in a timely and easy fashion.

SUMMARY

According to one aspect of the present invention, a novel foot measuring application is described. The application generally involves a software application program running on a computing device that includes a built-in camera, or is coupled to a camera. The computing device may be capable of generating a "live view" of the image field of the camera when the camera function is turned on, also referred to as a "preview screen" or a "digital viewfinder." The computing device may also be capable of connecting to remote server computers, through TCP/IP or other internet protocols. The novel foot measuring application may generate dimensional data by comparing points on the target foot with a known measuring reference that is also in the camera field of view. In some embodiments, the application utilizes a sheet of standard-sized paper, such as Letter or A4, as a reference object. For example, the application may instruct a user to place a sheet of paper on the ground, place his or her foot on the paper (with or without socks or nylons), and then to use the built-in or coupled camera with the application running on the computing device to capture video (a series of images) of the target foot in the viewfinder within a prescribed zone of distance from the foot.

Certain embodiments may display an "augmented reality" indication of measurement in the preview screen, such as zones of different colors corresponding to different shoe sizes, overlaid under or around the target foot. For example, such indications may be provided in order to give the user feedback about the dimensions being generated by the application's size-analyzing process. These measurement overlays are "target relative" in that they appear to be fixed relative to the target foot and paper reference, even if the camera or computing device are moved (e.g., if the overlays moved when the computing device moved, the overlays would be defined as "device relative"). Such embodiments better replicate the experience of current traditional physical foot measuring methods. Specifically, the user may remeasure the foot based on the user's perception of the process accuracy, and understand during the live process how and why the resulting foot size measurement was generated.

DETAILED DESCRIPTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising." when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

New foot measuring applications for determining the size of feet and appropriate corresponding shoe sizes are discussed herein. In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below. The present invention will now be described by referencing the appended figures representing preferred embodiments.

Figure 1:
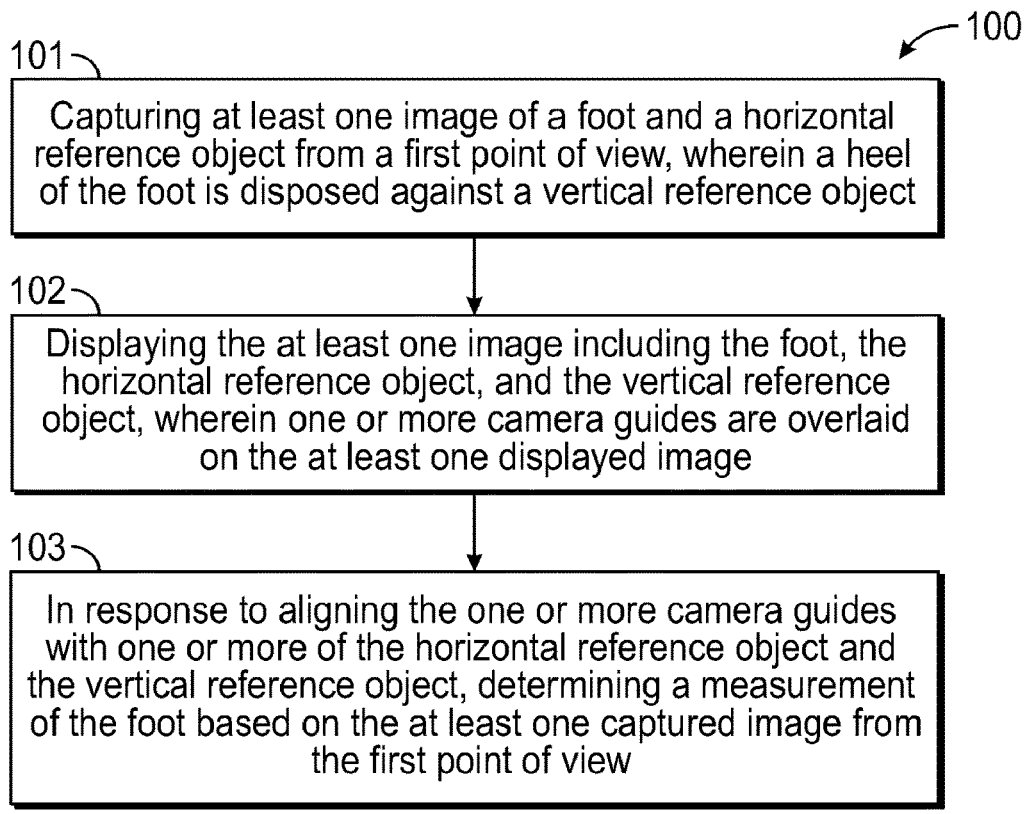
FIG. 1 illustrates an exemplary process for determining measurement of a foot based on at least one captured image of a foot and a horizontal reference object.

FIG. 1 illustrates an exemplary process 100 for determining measurement of a foot based on at least one captured image. For example, as discussed further herein, process 100 may begin with a step (not shown) of launching an application on a computing device including a camera, such as a smartphone or tablet computer. In some embodiments, process 100 may include a step 101 of capturing at least one image of a foot and a horizontal reference object from a first point of view, where a heel of the foot is disposed against a vertical reference object. Furthermore, process 100 may include a step 102 of displaying the at least one image including the foot, the horizontal reference object, and the vertical reference object, where one or more camera guides are overlaid on the at least one displayed image. At least the capturing and displaying at steps 101-102 are discussed in detail with respect to FIG. 2.

Figure 2:
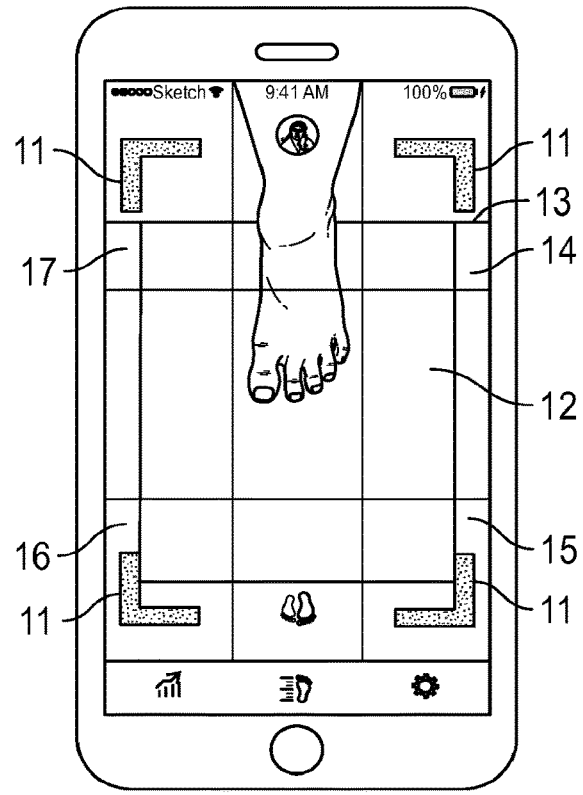
FIG. 2 illustrates a screen view of the application, viewable by the user, depicting a first step in the measurement process and the alignment guides for the reference object.

Referring now to FIG. 2, a screen view of the application is depicted. The screen view depicted in FIG. 2 includes a representation of an image preview screen of the application, which may be displayed when the application is launched on the computing device. In some embodiments, the application indicates four corner alignment guides 11 for the reference paper object 12. In some embodiments, the application will first prompt the user to select the reference object from a menu of choices. For example, a menu may include options such A4-sized paper or Letter-sized paper. In this case, paper object 12 may represent a piece of white A4-sized paper. The program may further instruct the user to place the reference paper with a shorter edge against a wall corner 13. The program next instructs the user to place their foot on the paper with the heel against the wall. This instruction allows the program to determine the foot rear limit (e.g., the heel edge) since the actual rear limit will not be visible in the typical viewing angle, such as that depicted in FIG. 2. This viewing angle will be typical for both a user measuring someone else's foot, and for a user measuring their own foot (objects in the screen view may be rotated 180 degrees, depending on whether the user is measuring their own foot). The program may assume that the foot rear limit is collinear with wall corner line 13.

In some embodiments, a first step in effectively measuring a target foot involves establishing the location of the reference paper. Accordingly, the four corners of the reference paper must be established. The camera field of view may be divided into nine grid blocks, and the user is instructed to manipulate the camera such that each corner of the reference paper lies within grid blocks 14, 15, 16, and 17. The corner guides 11 may be displayed for user guidance only, and the program may not require that the four corners be precisely aligned with these guides, which may increase usability. The grid blocks, and corner search in specific blocks, are a key part of the overall measurement algorithm and greatly reduce errors and process time.

In order to find the paper corners within the four grid block areas, the invention applies aspects of "corner detection" algorithms established in the field of computer vision. A two-step process may be utilized to detect corner separation between the paper and the floor. In a first step, the invention converts the color image data into grey-scale with average intensity values. The second step includes down-sampling, which may include reducing resolution but maintaining key details of the data.

Specifically, during the first step of the algorithm, red-blue-green (RBG) image data is converted into a hue-saturation-value (HSV) color space, with intensity values determined based on averaging three different HSV values. In some embodiments, the camera may utilize a Behr-type sensor with double the number of green detection elements than red and blue elements. Thus, the program may only account for half of the green values. In turn, this process ignores and/or removes all color information and converts the data into "brightness" values across all different color values. During the second step, the HSV values are then transformed into a vector space through computations of first and second order differentials to determine velocity and acceleration of change in HSV value. In areas where there is the most change in HSV value, the program maintains more data, and where there is less change in HSV value, the program increases the rate of averaging of HSV values. This "binarization" process maintains more data along the edges of the paper. The paper corners are then determined based on the intersections of two edges, and the vertex of a corner is determined as the intersection of the two edges at that corner.

In some embodiments, the computing device may be a mobile smartphone or tablet. The image processing described above may be performed based on a video feed from at least one camera included within or coupled to the device. Typically, such devices may generate video at a rate of thirty frames per second. The corner-detection process described above may thus be performed on each successive video frame until the program determines that (i) four corners have been located, and (ii) there is one corner in each of grid blocks 14, 15, 16, and 17. In some embodiments, when a corner has been detected within a given block 14, 15, 16, or 17, the reference guide corner 11 in that corresponding grid block will change color in the camera preview screen. This color change provides the user with feedback on the progression of the overall process. If there are problems at this step (e.g., one or more corners are obscured from the camera's view, are crumpled or distorted, or if there is no paper in the camera's view), the program will continue to run the corner detection process on succeeding video frames until a defined time limit is reached. Once such limit is reached, the program may prompt the user to confirm that all reference paper corners are visible in the view screen of the camera.

Figure 3:
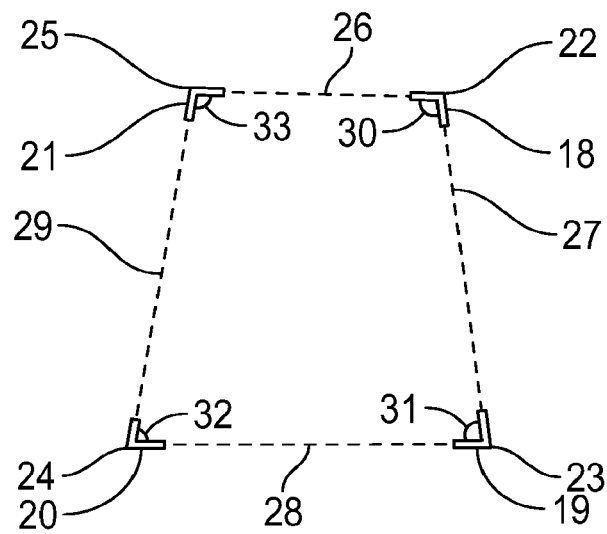
FIG. 3 illustrates a visualization of the application process, depicting the measurement algorithm processes of corner and vertex detection, reference establishment, and perspective transformation.

Referring back to FIG. 1, process 100 further includes a step 103 of, in response to aligning the one or more camera guides with one or more of the horizontal reference object and the vertical reference object, determining a measurement of the foot based on the at least one captured image from the first point of view. At least the aligning and determining at step 103 are discussed in detail with respect to FIGS. 2-5. Referring now to FIG. 3, a visualization of the application process is depicted, including measurement algorithm processes of corner and vertex detection, reference establishment, and perspective transformation. FIG. 3 illustrates detected corners 18, 19, 20, and 21 given the perspective view of the camera. The view in FIG. 3 would not typically be displayed to a user, but instead, is provided to illustrate the internal processes of the program. In some embodiments, a typical viewing angle of the camera will likely not be directly over the reference paper, and thus, the paper corners will not appear to be square ninety-degree corners due to perspective effects. These non-square corners are acceptable for the program as the corner-detection goal is to determine the corner vertices (vertex points) 22, 23, 24, and 25. Next, the program may establish straight lines 26, 27, 28, and 29 between the vertices. After establishing the straight lines, the program may calculate the angles 30, 31, 32, and 33 between the straight lines so that the program can perform a perspective transform from a given orientation to a known orientation. By assessing whether an angle is obtuse or acute, and the respective degrees of the angles, the program can determine the degree to which image data should be corrected for perspective effects. Furthermore, the algorithm of the program may error-check that angles 30, 31, 32, and 33 add up to 360 degrees.

Figure 4:
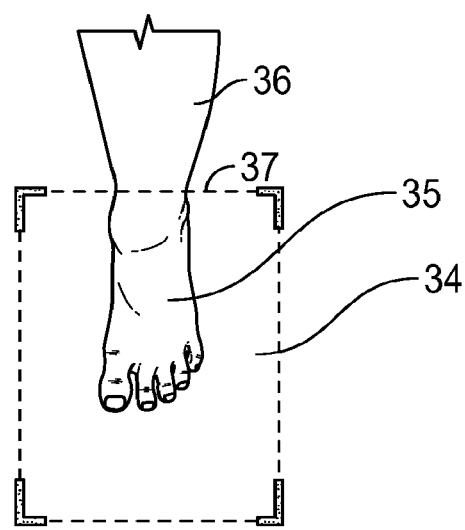
FIG. 4 illustrates a visualization of the application process, depicting a measurement algorithm of target foot detection.

FIG. 4 illustrates the result of the perspective transformation process described in FIG. 3. The view in FIG. 4 would not typically be displayed to a user, but instead, is provided to illustrate the internal processes of the program. In some embodiments, a rectangle with square angles 34 is generated. For example, the program may establish side lengths of the squared reference frame rectangle based on the known dimensions of standard reference paper sizes (e.g., 8.5"×11" for Letter-sized paper), which are defined in the program. The program may also correct the image data within the reference rectangle, including the target foot. In one embodiment, correction of the image data includes "stretching" the image data in order to establish the reference frame having the predefined dimensions of the paper reference 12. In a next step, the program may look for the foot inside of the reference frame by running an "edge-detection" process similar to the corner-detection process described above. Based on a similar process of image processing and binarization, the program may establish the edges between the foot 35 and the paper inside of the area of the reference rectangle. The edge detection performed on the foot is more sophisticated than the edge detection performed on the paper. For example, the edge detection performed on the foot may handle minor shadows extending from the mid or rear of the foot. The foot edge detection may iterate on the region inside the paper using a successively varying gradient threshold to delineate between foot and shadow. Typically, the visual field of the video frame will include the leg 36 extending from the foot. The program may trim the edge-detected object 35 of contents beyond the back edge 37 of the reference rectangle. In one embodiment, edge 37 is collinear with wall-floor corner line 13 described above. In turn, this process effectively trims the leg form 36 and retains the relevant foot size information. This trimming is appropriate since the user was previously instructed to align the reference paper to the wall-floor corner 13, and to place their heel against this corner.

Figure 5:
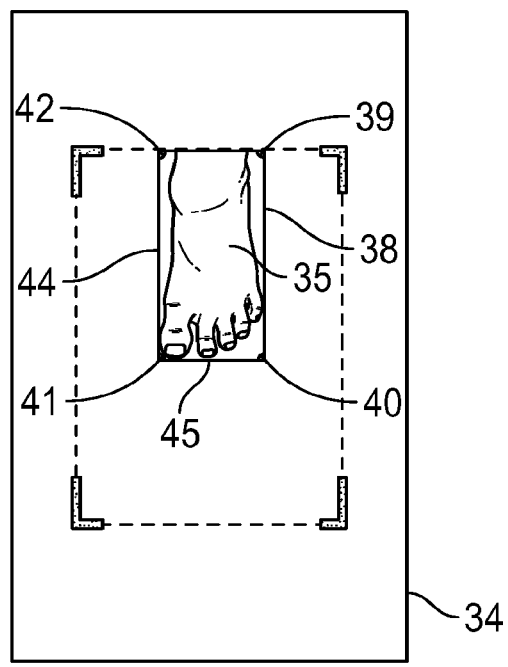
FIG. 5 illustrates a visualization of the application process, depicting a measurement algorithm of target foot boundary determination, rotation detection and correction, and object measurement.

Referring now to FIG. 5, the program may establish an object frame 38 around the foot object 35. The view in FIG. 5 would not typically be displayed to a user, but instead, is provided to illustrate the internal processes of the program. In some embodiments, the program may determine the angles 39, 40, 41, and 42 on the object frame to determine the characteristic (or major) vector of the frame, and therefore, of the foot. Next, the program may determine whether the characteristic vector is orthogonal to the minor axis of the reference frame 34, and therefore, whether the characteristic vector is orthogonal to the paper. As a result, these algorithmic steps determine if the foot is rotated relative to the paper. If the program determines that object frame 38 is rotated beyond a set of preprogrammed dimensional tolerances, then the program will transform the image data such that object frame 38 is rotated back to "straight" (e.g., with characteristic vector orthogonal to the minor axis of reference frame 34). At this point, the program is ready to start the size analysis of the video frames.

In one embodiment, the program may perform size analysis based on the size of the object frame 38. For example, length 44 may represent a foot length, and width 45 may represent foot width. These measurements may be determined relative to the known measurements of the edges of the reference frame 34. As a first step, the program may perform filtering to disregard results that are too extreme. For example, filtering may allow the algorithm to be more efficient, as the program does not need to run the rest of the analysis if the initial analysis returns gross errors. Gross error filtering may include discarding results for length 44 or width 45 that are too small (e.g., less than the size of the smallest infant shoe size). Where the non-conforming results are filtered out, results for length 44 and width 45 are compared to determine whether the resulting aspect ratio is within the preprogrammed range of possibility for a foot. In some embodiments, when the results finish the gross error checking, a visual indication on the camera preview screen may provide an indication to the user that the foot has been detected in the overall process.

In one embodiment, the program maintains results that are not filtered out and determines a final result based on the average of a preset X multiple number of measurements. For example, in some embodiments, five results are averaged. The program will run this final average analysis when X consecutive video frames generate measurements, for both length 44 and width 45, within a preset tolerance Y of each other. For example, in some embodiments, the tolerance may be set at 5 mm. Depending on the application and device used (e.g., depending on camera specifications), in some embodiments, the program may utilize more or less consecutive values, may use a greater or lower tolerance than 5 mm, and/or may use a different averaging methodology (e.g., accepting any five values within the accepted 5 mm tolerance within a ten measurement block of values).

Figure 6:
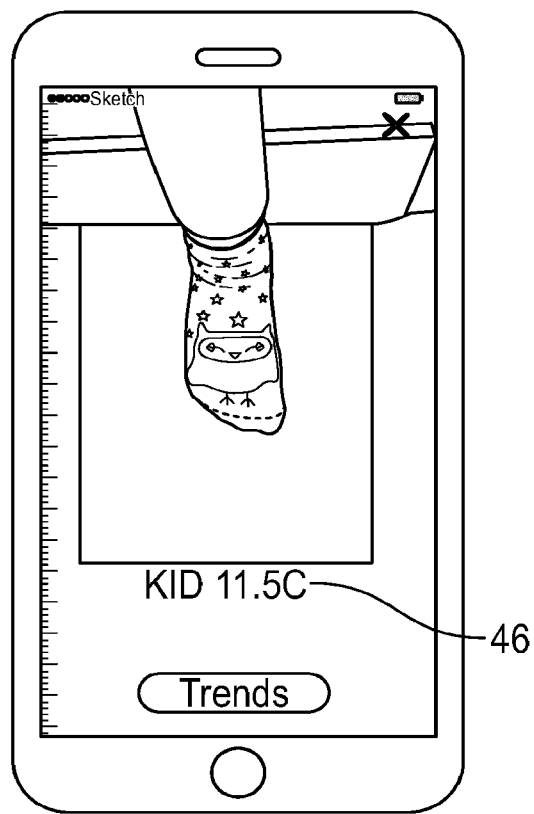
FIG. 6 illustrates a screen view of the application, depicting the measurement analysis result that may be viewable by a user.
Figure 7A:
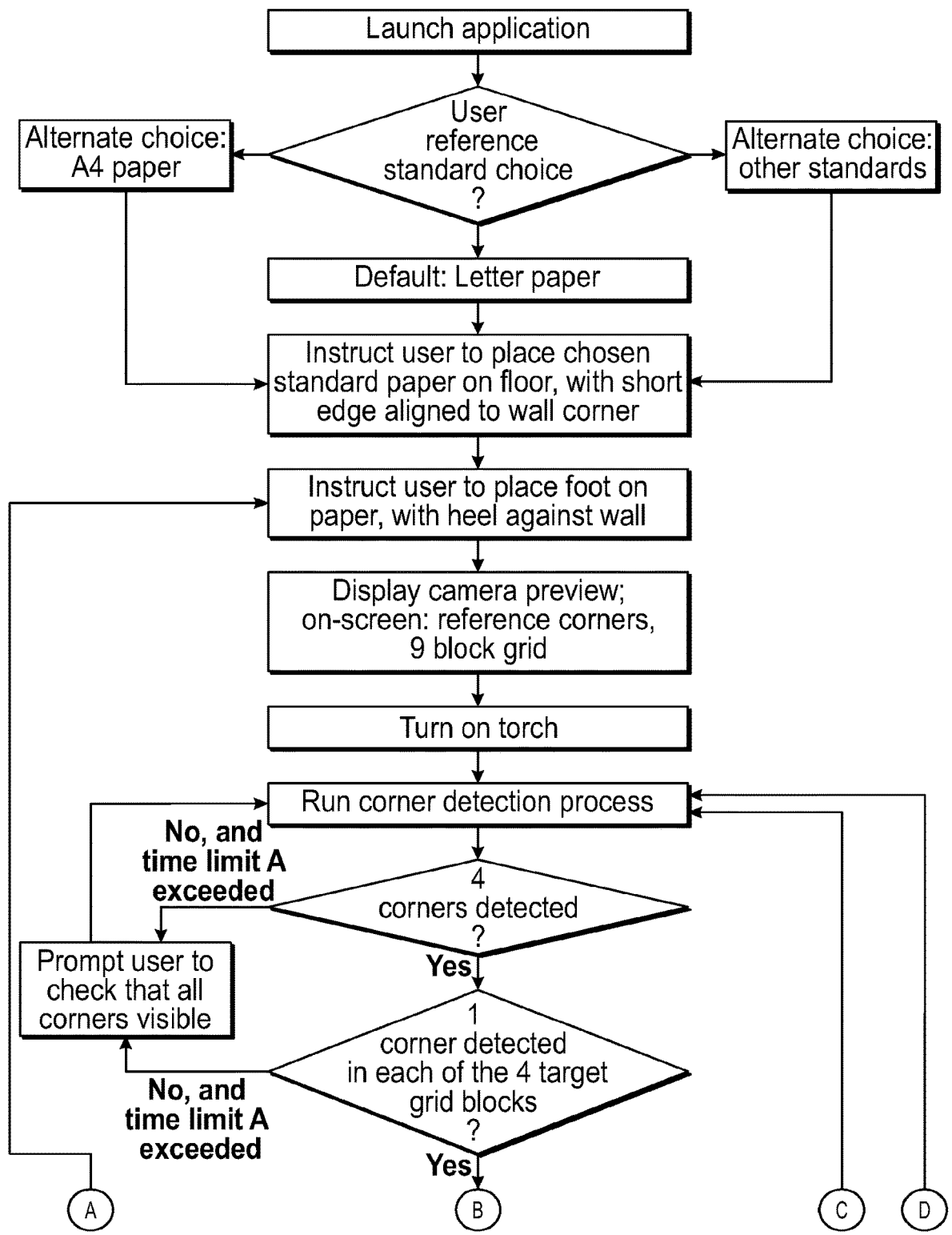
FIGS. 7A-7D illustrate a measurement process implemented by the foot measuring and sizing application.
Figure 7B:
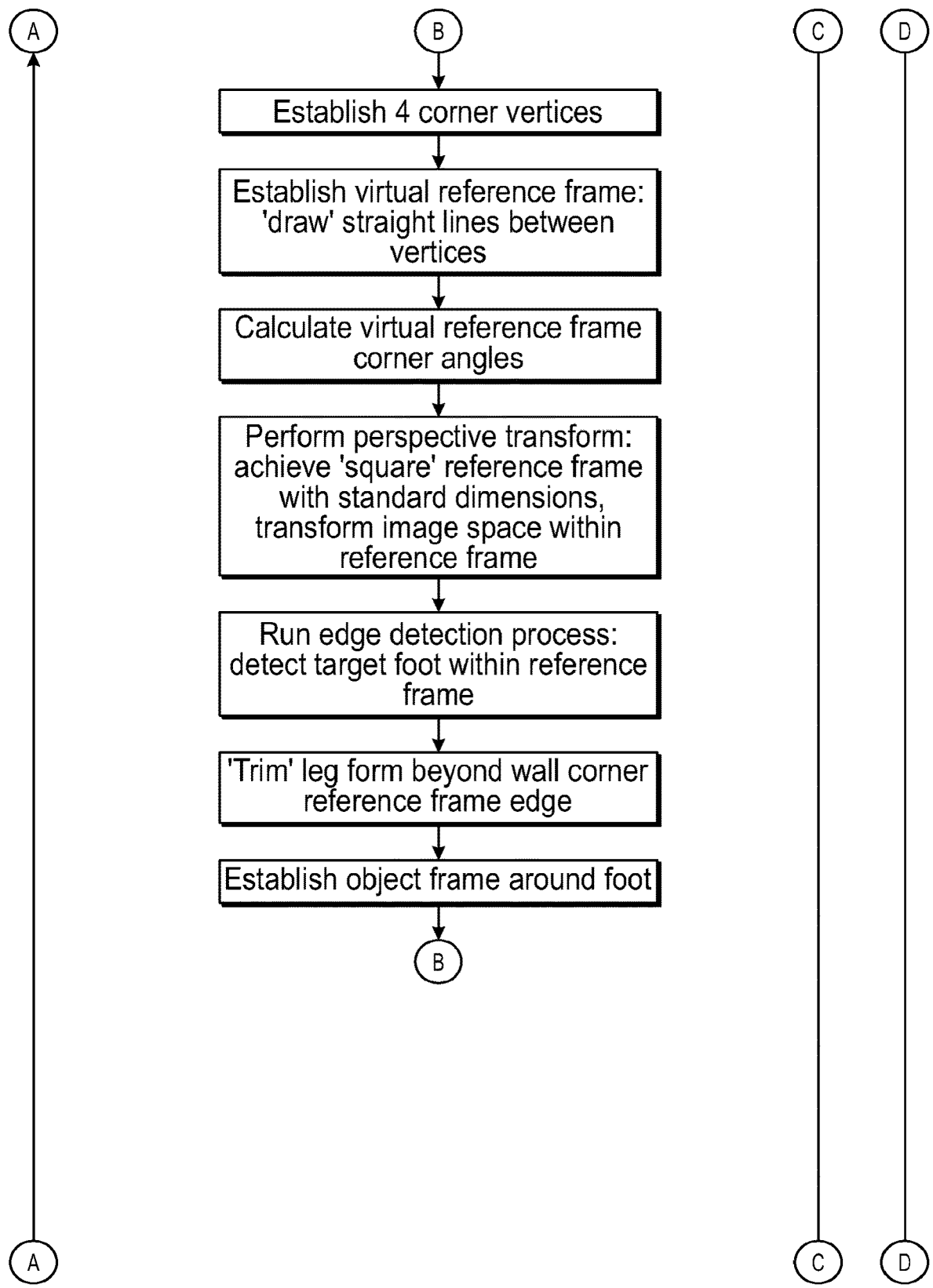
Figure 7C:
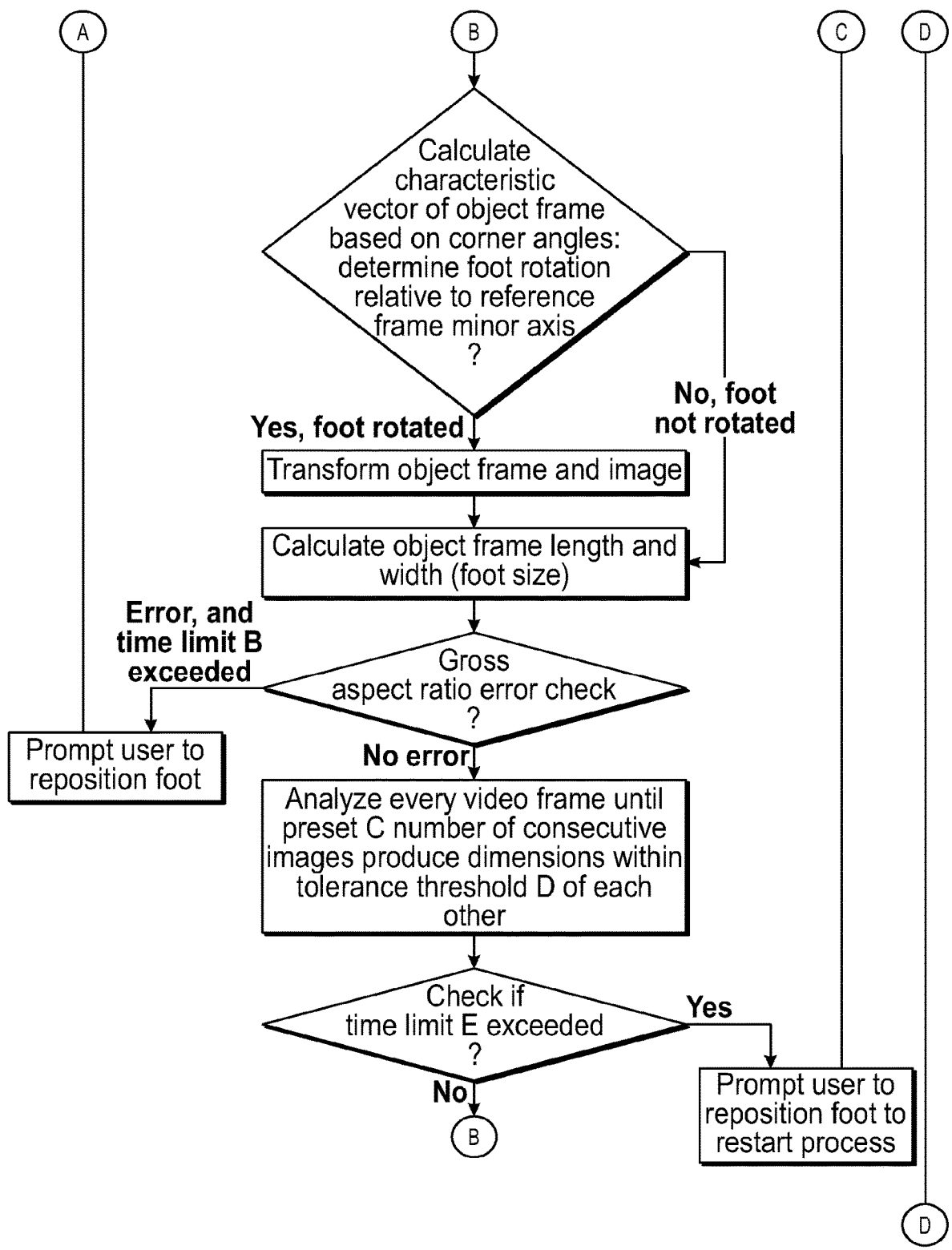
Figure 7D:
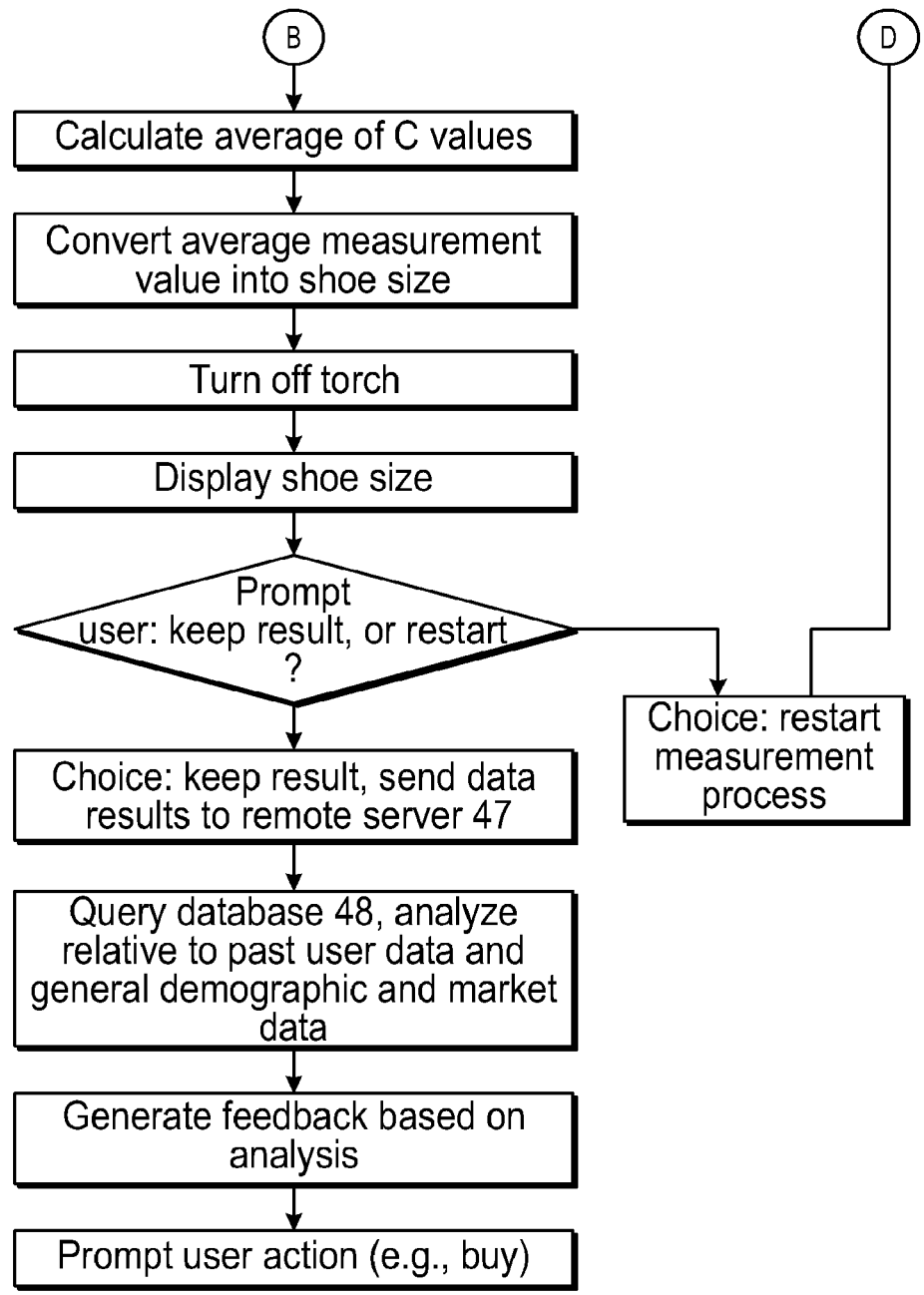

Referring now to FIG. 6, the program may display size information 46 within a preview screen. In one embodiment, the program may convert final averaged values into shoe sizes based on preprogrammed shoe size information. For example, a database within the program may maintain sizes and corresponding dimensional values.

In some embodiments, the program may instruct the user to wear a sock before stepping on the paper. Although, the processes described above may function independent of whether a user is wearing a sock, the use of a sock in this embodiment may, for example, assist in preventing a foot from sticking to the reference paper (e.g., due to moisture on the foot).

Furthermore, while running the video analysis, the program may activate a built-in flashlight continuously (sometimes referred to as "torch" mode) until a final value is determined. This extra light source may assist to mitigate extreme lighting, such as prominent shadows and glare, that can affect the analysis. For similar reasons, the program may instruct the user to choose a measurement environment with even lighting.

In some embodiments, the program may be run locally, without requiring access to remote server computations. This client-side calculation may significantly improve responsiveness of the application and reduce latency, compared to a solution that would rely on remote server-side computations. In practice, under the proper conditions as described above, the analysis may typically be performed by the computing device in less than five seconds and may be perceived as relatively "instantaneous" to the user.

FIGS. 7A-7D illustrate a representative flow chart of an exemplary embodiment of the foot measuring application program, depicting the steps and logic involved in the process. In general, one or more of the steps described above are represented in this flow chart. As described above, the client-side application does not need to access the remote server 47 in order to analyze the foot size. In one embodiment, the remote server 47 may be accessed for ancillary functions.

Figure 8:
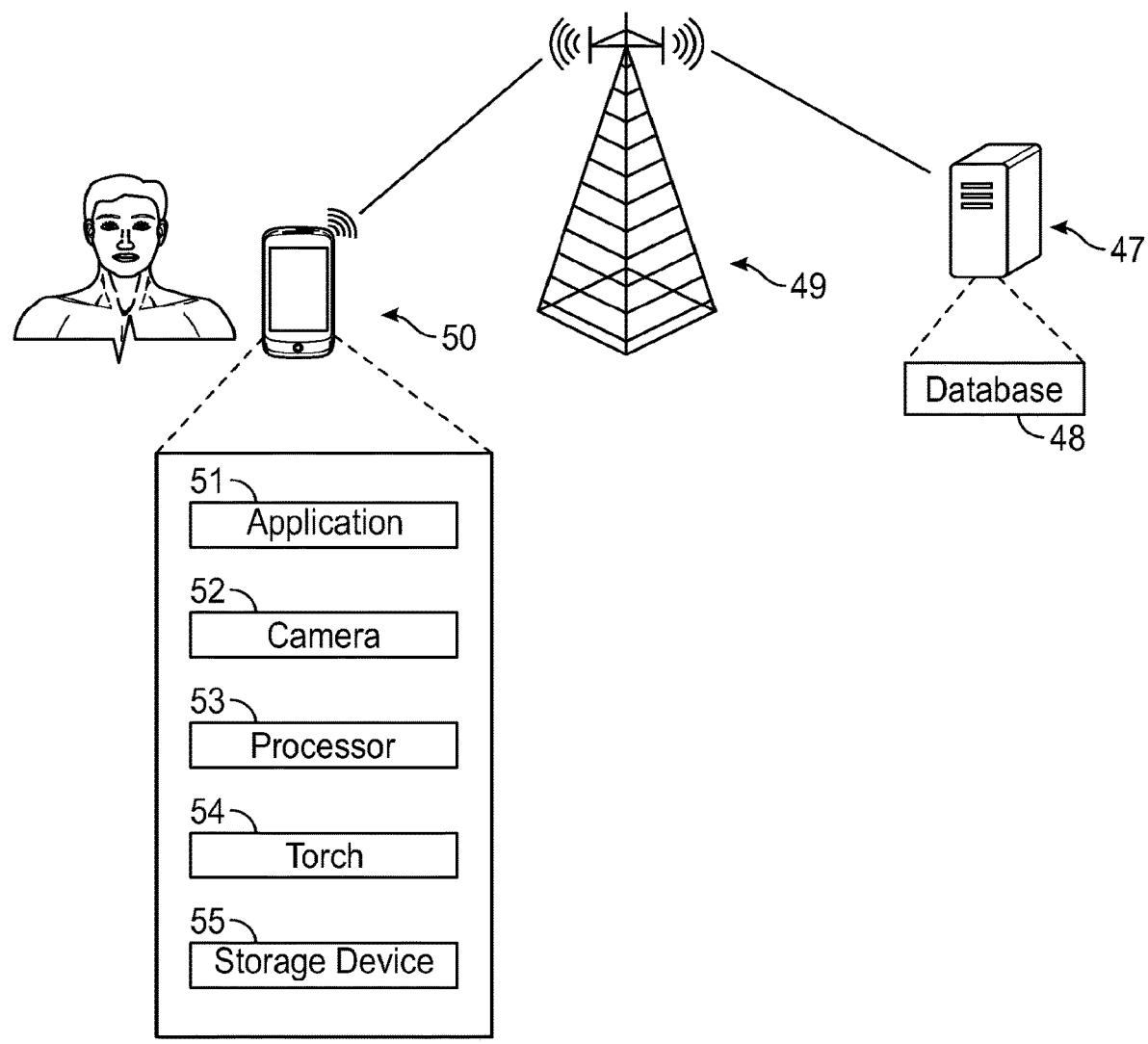
FIG. 8 illustrates a diagram depicting a local client computing device and a remote server computer utilized during a measurement process.

Referring now to FIG. 8, remote server 47 may provide additional benefits to the user, such as being able to display information including data relative to past measurement results and population data. For example, such information may be retrieved by accessing server-side databases 48. In one embodiment, remote server 47 is accessed wirelessly through internet, cellular, or other wireless networks 49. However, all core novel foot measuring functionality may occur within the application program on the client-side computing device 50, as seen in FIGS. 7A-7D. As discussed above, this client-side functionality may significantly improve the responsiveness and speed of the application, and may also ensure that core functionality of the application is available to the user even when the computing device is not connected to the internet, network 49, or other means of communication. FIG. 8 further illustrates the core functionality required on the client computing device side in some embodiments, including application 51, camera 52, processor 53, torch 54, and storage device 55. For example, processor 53 may be required to perform the analysis described in this preferred embodiment, and to run the software application 51 as described. As another example, the local storage 55 may be required to buffer data as part of running application 51, and to store data and results in the event there is no network connection 49 available. In some embodiments, connection to remote server 47 is not a part of the functionality of the application.

Figure 9:
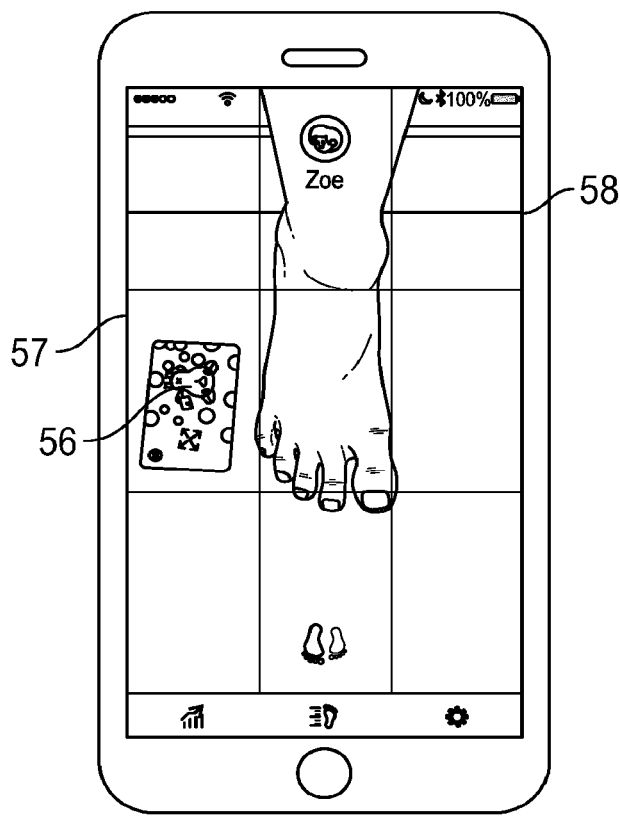
FIG. 9 illustrates a screen view of the foot measuring and sizing application including an alternate reference object.

Referring now to FIG. 9, in some embodiments, a heel of the foot is placed against a wall, but the foot is not resting on top of a piece of reference paper. For example, an alternate reference object 56 of known size may be placed next to the foot. An alternate reference object 56 may include objects having known sizes, such as credit card 56. The embodiments discussed with respect to FIG. 9 may function similarly to those discussed with respect to FIGS. 1-8. For example, reference object 56 may correspond to the horizontal reference object at step 101 of FIG. 1. Furthermore, the program may detect the reference object 56 through a similar edge detection process as discussed above, within a prescribed area indicated on the screen, such as the box 57 as demarcated by the thin white lines. The program may detect the boundary edge 58 between the wall and floor through a similar process of edge detection. The program may then detect the foot in a process similar to the embodiments described above, for example, by determining a virtual boundary box around the foot. The program may determine the dimensions of the foot by comparing to the known dimensions of the reference object.

In some embodiments, the method for identifying the foot in the field of view can be determined by other means. For example, identification may be based on analysis of skin color compared to the color of the reference paper. Another alternative identification is to detect subcutaneous blood flow through, for example, "Euler methodology." in order to distinguish the skin of the target foot from the reference paper.

Figure 10:
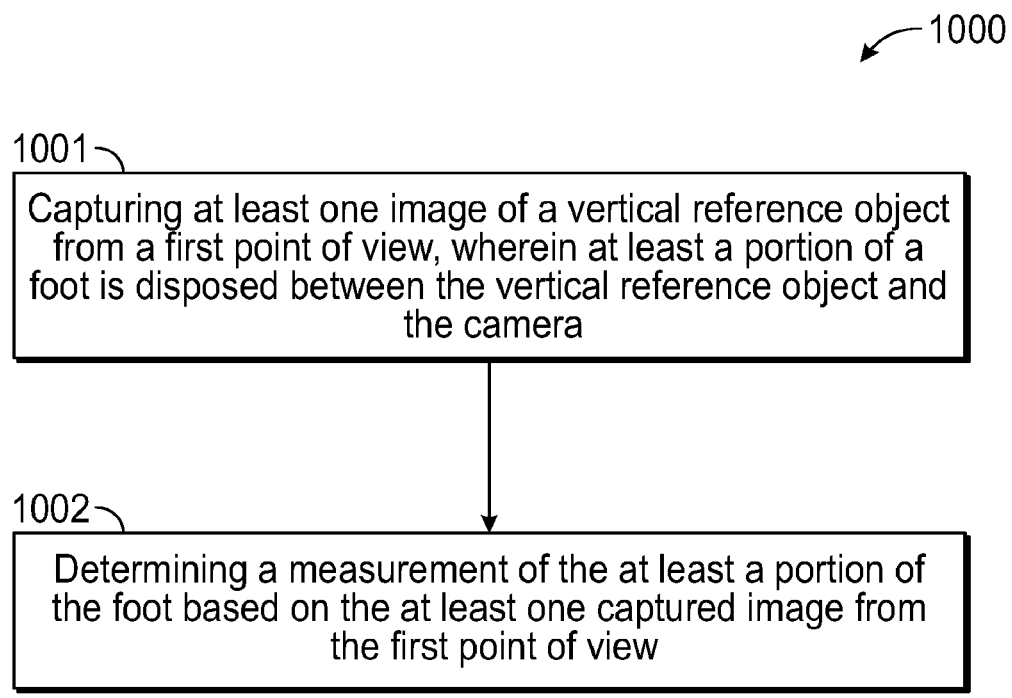
FIG. 10 illustrates an exemplary process for determining measurement of a foot based on at least one captured image of a vertical reference object.

FIG. 10 illustrates an exemplary process 1000 for determining measurement of a foot based on at least one captured image of a vertical reference object. Similar to that discussed with respect to FIG. 1, for example, process 1000 may begin with a step (not shown) of launching of an application on a computing device including a camera, such as a smartphone or tablet computer. In some embodiments, process 1000 may include a step 1001 of capturing at least one image of a vertical reference object from a first point of view, wherein at least a portion of a foot is disposed between the vertical reference object and the camera. At least the capturing and determining steps 1001-1002 are discussed in detail with respect to FIG. 11.

Figure 11:
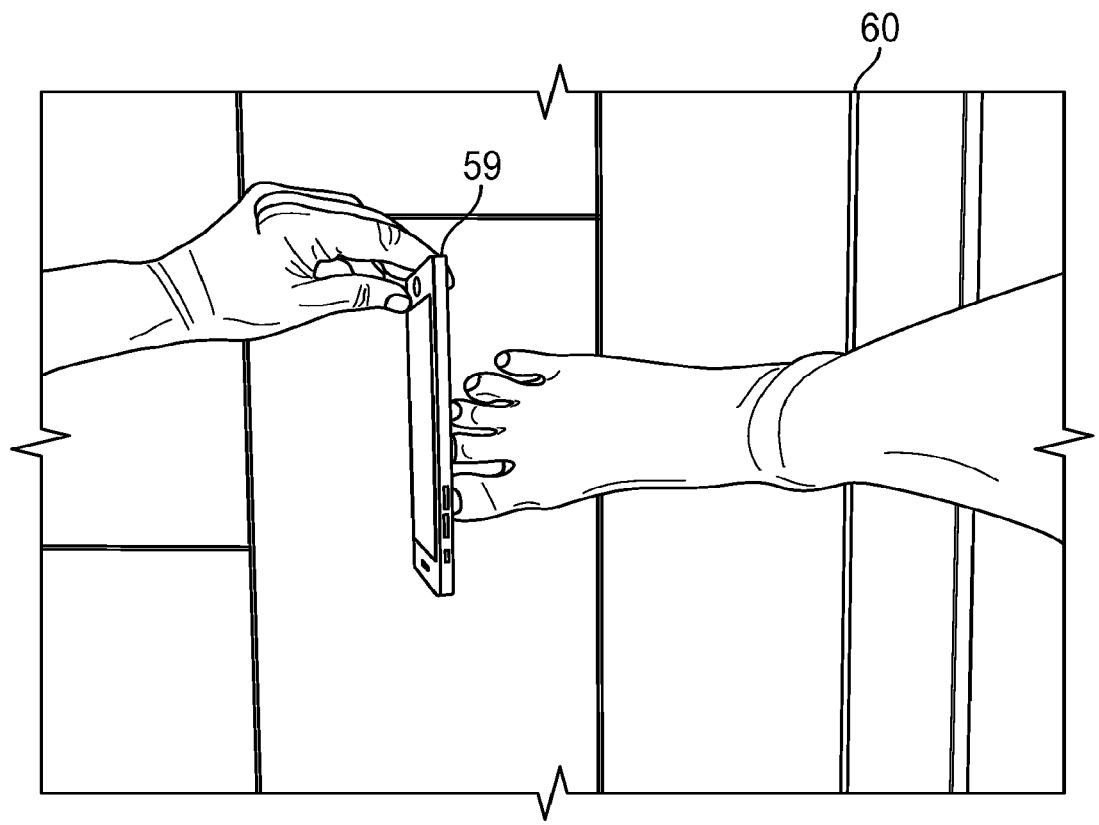
FIG. 11 illustrates an alternate embodiment including a computing device positioned without a horizontal reference object.

Referring now to FIG. 11, an embodiment including a computing device 59 positioned without a reference object is depicted. In some embodiments, a portion of the foot (such as the heel of the foot as seen in FIG. 11) is placed against a wall, and a computing device 59 (e.g., a "smartphone") is placed on the floor with the forward-facing surface of the device touching the forward-most toe of the foot. In this orientation, the length of the foot would be measured. Alternatively, the length can be measured with the toe against the wall and device 59 placed on the ground against the heel. Furthermore, the width of the foot can be measured by placing either side of the foot against the wall, and placing device 59 against the opposite side of the foot.

In one embodiment, as illustrated in FIG. 11, no reference object is needed. In this embodiment, the forward-facing surface of the camera in this case is defined as the surface with the primary camera, which is typically the surface opposite from the screen. To determine the dimensions of the target foot, the program relies on the focusing feature of the camera, which determines the distance of the camera from the wall through a range-finding process. Depending on the computing device, the user may need to select the wall as the focus subject, for example by touching on the touchscreen to direct the camera to focus on the wall area. In addition, the user may need to select the "focus lock" feature of the device, to maintain a focus on the wall, depending on the specific device.

In order to accurately measure the distance to the wall that best represents the dimension of the foot (either length or width), the camera may be required to be "square" to the wall, such that the forward-facing camera surface is coplanar with the wall. In one embodiment, built-in sensors of the device, such as gyroscopes, will determine if the device is orthogonal to the ground plane. If the camera is tilted relative to the ground plane, the program will prompt the user to straighten the smartphone, for example, through on-screen directions. To determine if the camera is tilted relative to the wall plane, the device may utilize a similar edge detection process, as described in the embodiments above, to determine the wall-to-floor boundary line 60. The program may then determine if this line is angled or horizontal, and may prompt the user to turn the smartphone if needed in order to achieve a horizontal line. Once the device orientation is coplanar to the wall within preprogrammed tolerances, the distance to the wall is recorded and the program is then able to calculate the foot dimension, and thus, appropriate shoe size. The program may then follow a similar process as in the embodiments described above, for example, by displaying the foot dimension onscreen and optionally communicating with remote servers.

Figure 12:
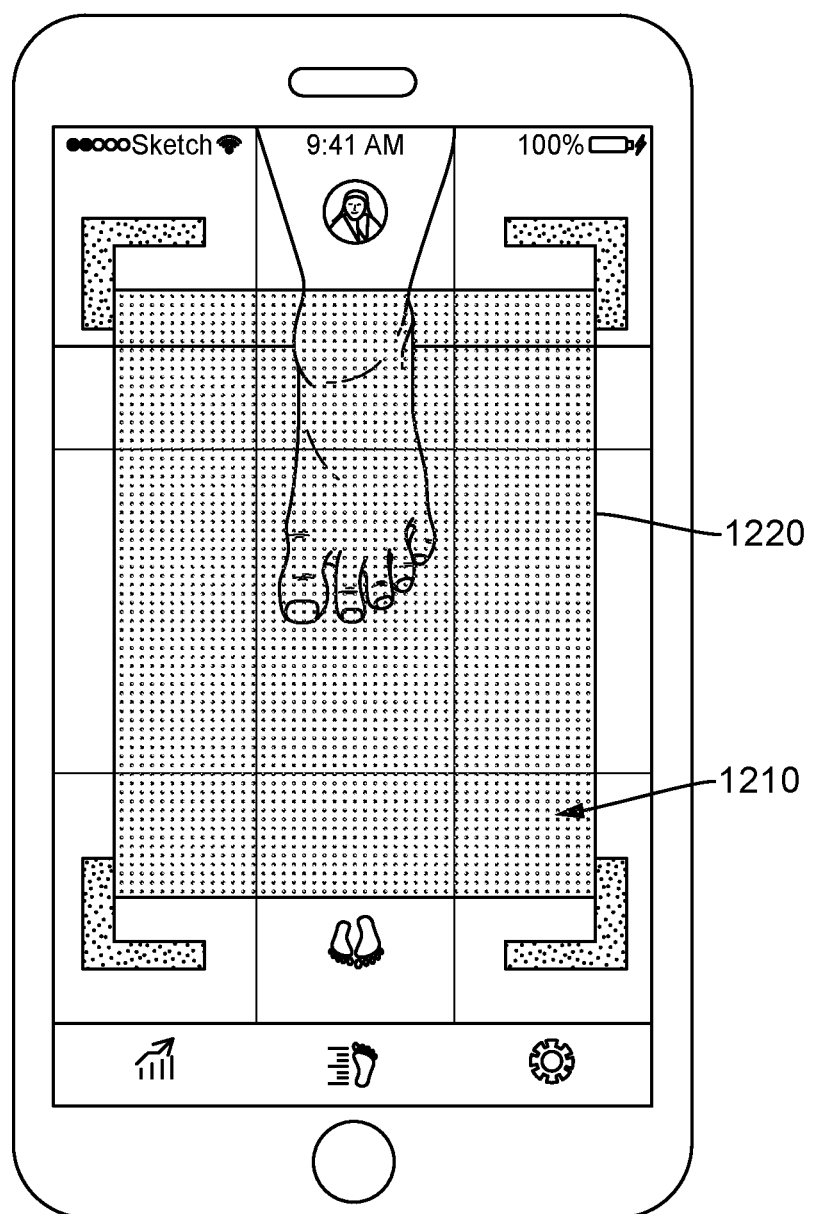
FIG. 12 illustrates a screen view of the application, viewable by the user, depicting a first step in the measurement process and reference dots.

In another embodiment, as shown in FIG. 12, without the use of a reference object, spatial depth sensors are used. In particular, this embodiment may be implemented when the application program is running on a mobile computing device that incorporates sensors that measure spatial depth. Typically, depth-sensing sensors incorporate a methodology known as time-of-flight infrared laser dot metrology (however, in other examples other techniques are possible, such as parallax techniques using multiple cameras, for example). Such sensors typically utilize an infrared emitter that projects a series of infrared dots 1210 onto objects in the field of view 1220, as shown in FIG. 12, and at least two cameras that can detect these dots 1210. One or more algorithms determine the depth of the contours and objects in the field of view, based on the time-of-flight of the reflected dot light. This depth information allows the device to determine the size and shape of a detected object, based on the calculated absolute depth values. As related to this example, these depth-sensing sensors allow for the size and shape of a foot to be determined by the program, and for the resultant foot size results to be displayed as discussed above in the process for determining measurement of a foot based on at least one captured image of the foot. On some smartphones and mobile devices with one or more depth-sensors on the rear-face of the device, the side of the device opposite from the primary device screen facing the user, the user would direct the device as described above in the process for determining measurement of a foot based on at least one captured image of the foot. For example, the user may direct the device as shown in FIG. 12, and be guided by onscreen prompts. On devices in which one or more depth-sensors are on the front-face, the side of the phone facing the user, the user must turn the primary device screen away towards the foot being measured in order to utilize the program to size the foot. In these cases, the program may guide the user by providing indications to the user of a measurement completion through other device means, such as an audible tone or a brief flashing of the rear-side flash. The user would then be able to turn the device screen back towards themselves in order to see the measurement result.

Although a variety of examples are used herein to describe embodiments within the scope of the appended claims, no limitation of the claims should be implied based on particular features or arrangements in such examples. Accordingly, one of ordinary skill in the art will be able to use these examples to derive a variety of implementations. Although subject matter may have been described in language specific to examples of different structures and processes, it is to be understood that the subject matter defined in the appended claims is not necessarily limited to these structure and processes. For example, such functionality can be distributed differently or performed in components other than those identified herein. Rather, the features are disclosed as examples of components of systems and methods within the scope of the appended claims.

What is claimed is:

1. A method for measuring an object, comprising:
   displaying, by a mobile computing device, at least one image of a portion of a user body part, and a plurality of reference dots from a point of view, wherein one or more camera guides are overlaid on the display of the at least one image;
   aligning, by the mobile computing device, the one or more camera guides with the portion of the user body part; and
   determining, by the mobile computing device, a measurement of the portion of the user body part based on the at least one image and the plurality of reference dots from the point of view.

2. The method of claim 1, wherein the portion of the user body part comprises a foot.

3. The method of claim 1, further comprising:
   generating, by the mobile computing device, a squared reference frame based on the at least one image; and
   performing, by the mobile computing device, edge detection on the squared reference frame to establish edges of the portion of the user body part.

4. The method of claim 3, further comprising delineating, by the mobile computing device, between the portion of the user body part and at least one shadow associated with the portion of the user body part using a successively varying gradient threshold.

5. The method of claim 1, wherein determining a measurement of the portion of the user body part further comprises:
   performing, by the mobile computing device, edge detection on the at least one image to detect a body part object;
   generating, by the mobile computing device, an object frame based on detecting the body part object; and
   performing, by the mobile computing device, a size analysis based on a size of the object frame to obtain at least one measurement.

6. The method of claim 5, wherein the at least one measurement comprises at least one length of the object frame and at least one width of the object frame.

7. The method of claim 1, wherein the portion of the user body part is disposed against a vertical reference object, and wherein the at least one image of the portion of the user body part is displayed with the vertical reference object.

8. The method of claim 1, wherein the plurality of reference dots comprises a series of infrared dots projected into at least a portion of the point of view.

9. The method of claim 1, further comprising:
   projecting, by a depth sensor of the mobile computing device, the plurality of reference dots; and
   detecting, by at least one camera in the mobile computing device, at least a portion of the plurality of reference dots.

10. The method of claim 1, wherein determining the measurement of the portion of the user body part includes:
    determining, by the mobile computing device, a depth of contours of the portion of the user body part in the at least one image based on a time-of-flight measurement determined based on at least a portion of the plurality of reference dots;
    calculating, by the mobile computing device, at least one absolute depth value based on the depth of contours of the portion of the user body part; and
    calculating, by the mobile computing device, a size and a shape of the portion of the user body part based on the absolute depth value.

11. A mobile computing device, comprising:
    a processor;
    a camera;
    a memory storing instructions that, when executed by the processor, cause the mobile computing device to:
       display at least one image comprising a user body part and a plurality of reference dots from a point of view, wherein one or more camera guides are overlaid on the at least one image;
       determine an alignment of the one or more camera guides with the user body part and the user body part; and
       determine a measurement of the user body part based on the at least one image and the plurality of reference dots from the point of view.

12. The mobile computing device of claim 11, wherein the user body part comprises a foot.

13. The mobile computing device of claim 11, wherein the instructions, when executed by the processor, further cause the mobile computing device to:
    generate a squared reference frame based on the at least one image; and
    perform edge detection on the squared reference frame to establish edges of the user body part.

14. The mobile computing device of claim 13, wherein the instructions, when executed by the processor, further cause the mobile computing device to delineate between the user body part and at least one shadow associated with the user body part using a successively varying gradient threshold.

15. The mobile computing device of claim 11, wherein the instructions, when executed by the processor, further cause the mobile computing device to determine a measurement of the user body part by:
    performing edge detection on the at least one image to detect a body part object;

generating an object frame based on detecting the body part object; and performing a size analysis based on a size of the object frame to obtain at least one measurement.

16. The mobile computing device of claim 15, wherein the at least one measurement comprises at least one length of the object frame and at least one width of the object frame.

17. The mobile computing device of claim 11, wherein the user body part is disposed against a vertical reference object, and wherein the at least one image of the user body part is displayed with the vertical reference object.

18. The mobile computing device of claim 11, wherein the plurality of reference dots comprises a series of infrared dots projected into at least a portion of the point of view.

19. The mobile computing device of claim 11, wherein:
the mobile computing device further comprises a depth sensor; and
the instructions, when executed by the processor, further cause the mobile computing device to:
project, using the depth sensor, the plurality of reference dots within the point of view of the user body part; and
detect, using the camera, at least a portion of the plurality of reference dots.

20. The mobile computing device of claim 11, wherein the instructions, when executed by the processor, further cause the mobile computing device to determine the measurement of the user body part by:
determining a depth of contours of the user body part in the image of the user body part based on a time-of-flight measurement determined based on the plurality of reference dots;
calculating at least one absolute depth value based on the depth of contours of the user body part; and
calculating a size and a shape of the user body part based on the absolute depth value.

* * * * *